United States Patent [19]

Garlen et al.

[11] Patent Number: 4,831,023

[45] Date of Patent: May 16, 1989

[54] WATER WASHABLE VEHICLES FOR TOPICAL USE

[75] Inventors: David Garlen, Summit, N.J.; Vivek Desai, Ronkonkoma, N.Y.

[73] Assignee: Thames Pharmacal Co., Inc., Ronkonkoma, N.Y.

[21] Appl. No.: 879,489

[22] Filed: Jun. 27, 1986

[51] Int. Cl.$^4$ .................. A61K 9/06; A61K 31/56; A61K 31/58

[52] U.S. Cl. .................. 514/169; 424/78; 514/169; 514/172; 514/179; 514/844; 514/846; 514/847; 514/873; 514/886; 514/887; 514/996

[58] Field of Search .............. 514/169, 172, 179, 844, 514/846, 847, 873, 886, 887, 996; 424/78

[56] References Cited

U.S. PATENT DOCUMENTS 4,457,910 7/1984 Van Cleave ................. 514/919

*Primary Examiner*—Shep K. Rose
*Attorney, Agent, or Firm*—Kirschstein, Kirschstein, Ottinger & Israel

[57] ABSTRACT

Anhydrous vehicles for topical use, e.g. for use with topically active pharmaceutical agents, including antibiotics, anti-fungal agents, anti-inflammatory agents, antihistamines, antipruritics and local anesthetics, comprise principally from about 60 to about 90% by weight of at least one glycol solvent and from about 2 to about 20% by weight etherified saturated fatty alcohol having a total chain length of from 20 to 216 carbon atoms. The vehicles are substantially free of water, greasy substances and fatty alcohols having less than 16 carbon atoms. The vehicles have a cream-like consistency and can also incorporate suitable compatible plasticizers, coupling agents, penetrants and the like.

22 Claims, No Drawings

WATER WASHABLE VEHICLES FOR TOPICAL USE

BACKGROUND OF THE INVENTION

1. Field of the Invention

The present invention relates to non-irritating, anhydrous cream vehicles suitable for medicaments having topical therapeutic activity and other dermatological applications.

2. Description of the Prior Art

Pharmaceutical agents effective in topical application, e.g., for treating dermatological conditions, generally must be incorporated into a suitable ointment, lotion or cream vehicle to promote uniform application and effective transdermal absorption.

Originally, most vehicles for topical medicaments were in the nature of greasy ointments which are not water washable and have a tendency to adhere to and stain clothing. Moreover, the greasy composition of many ointments actually inhibits the release and absorption of many topically active pharmaceutical agents.

As an alternative to ointments, water-based creams were developed which are water washable and non-staining, and yet provide satisfactory spreadability and adherence while not inhibiting the release of active ingredients admixed therewith. These aqueous creams, however, are not suitable for use with active ingredients which are water-decomposable. Furthermore, many of the aqueous creams of the prior art provide little or no occlusive coating to the treated area. In the case of certain topically active agents, such as anti-inflammatory steroids, therapeutic efficacy is substantially increased when the topical vehicle provides occlusion as well as adherence.

In order to combine the desirable unctuousness and pharmaceutical compatability of oil-based ointments with the water miscibility and lightness of aqueous creams, anhydrous water washable vases have been developed which do not adversely affect moisture-degradable ingredients, enable rapid release of the active agent and provide an occlusive coating for enhanced pharmaceutical activity. Such anhydrous creams are disclosed, for example, in U.S. Pat. Nos. 3,592,930 and 3,888,995. The specific cream vehicles described in the aforementioned patents consist primarily of propylene glycol and a saturated fatty alcohol having from 16 to 24 carbon atoms. Various plasticizers, coupling agents and penetrants are also taught as valuable additional ingredients.

While anhydrous creams disclosed in the prior art, e.g., the fatty alcohol/propylene glycol creams, are effective and have been commercially used for topical steroid preparations, they suffer from a number of drawbacks. These creams incorporate fatty alcohols having 16 or more carbon atoms, but commercially available $C_{16}$ to $C_{24}$ fatty alcohols contain as impurities significant amounts of unsaturated alcohols and alcohols having fewer than 16 carbon atoms. These short-chain alcohols are known irritants which may exacerbate rather than ameliorate the condition to be treated. Moreover, while propylene glycol is the vehicle of choice for many topically active pharmaceuticals, particularly steroids (the higher the propylene glycol concentration, the less need there is for anti-bacterial and anti-fungal preservatives), the propylene glycol concentration in the known anhydrous creams cannot normally be increased beyond about 70% without decreasing the viscosity of the cream to the point where it resembles a lotion.

In addition, the fatty alcohol component of the known anhydrous creams does not enhance the hydrophilic character of the total vehicle. Hence, the prior art anhydrous vehicles do not achieve maximum spreadability upon contact with skin moisture, which is an important factor in patient acceptance of any topical product.

SUMMARY OF THE INVENTION

Objects of the Invention

It is an object of the present invention to provide water-miscible, anhydrous cream vehicles for topical use which overcome the aforementioned drawbacks of the prior art.

Another object of the present invention is to provide vehicles as described above which are particularly suitable for use with topically active pharmaceutical agents.

An additional object of the present invention is to provide vehicles as described above which maximize glycol content while maintaining a cream-like consistency.

Still another object of the present invention is to provide vehicles as described above which are bacteria and mold resistant even in the absence of added preservatives.

A further object of the present invention is to provide vehicles as described above which are non-irritating to the skin and do not provoke allergic reactions even in sensitive individuals.

Still a further object of the present invention is to provide vehicles as described above which form excellent, long-lasting, occlusive coatings over the treated area.

Yet another object of the present invention is to provide vehicles as described above which promote rapid transdermal absorption of the active ingredients contained therein.

A further object of the present invention is to provide vehicles as described above which are compatible with a wide range of pharmaceutical agents, including steroids, antibacterial agents, antihistamines, anesthetics and fungicides.

Still another object of the present invention is to provide vehicles as described above which achieve maximum spreadability with an appearance and consistency that promote patient acceptance.

Brief Description of the Invention

In keeping with these objects and others that will become apparent hereinafter, the present invention resides, briefly stated, in cream vehicles for topical use, such as for use with topically active pharmaceutical agents, consisting principally of about 60 to about 90% by weight of one or more glycol solvents and about 2 to 20% by weight of one or more etherified fatty alcohols. Suitable additional plasticizers, penetrants, opacifiers, coupling agents and the like, comprising no more than a maximum of 38% by weight of the total composition of the vehicle, can also be utilized.

The vehicles of the invention are anhydrous, water-washable and compatible with a wide variety of active ingredients including steroids, antibacterial agents, antihistamines, anesthetics and fungicides. The high concentration of glycol solvent, especially propylene glycol, in the vehicles makes them highly bacteria and mold resistant, even in the absence of added preservatives. Because of the purity of the etherified alcohols used, which have a chain length of at least 20 or more carbon atoms, the concentration of irritating fatty alcohols of less than $C_{16}$ chain length is essentially zero.

DETAILED DESCRIPTION OF THE INVENTION

The anhydrous, water-miscible, nonstaining cream vehicles of the present invention comprise from about 60 to about 90% by weight of one or more glycol solvents, e.g., propylene glycol, dipropylene glycol, or polyethylene glycols having a molecular weight from 200 to 800; and from about 2 to about 20% by weight of one or more etherified fatty alcohols. The term "etherified fatty alcohols", as used herein, encompasses all straight chain, saturated fatty alcohols having chain lengths of from 16 to 24 carbon atoms which are etherified with two or more alkoxy or alkylene glycol monomers, dimers or polymers. Such etherified alcohols are commercially available from a variety of sources, including the "BRIJ" line of products from ICI Americas, Inc. (Wilmington, Del.), the "PROCAL CA" line from Protameen Chemicals, Inc. (Totowa, N.J.), the "EUMULGIN" products from Henkel Corp. (Hoboken, N.J.), and the "NIKKOL BB" products from Nikko Chemicals (Tokyo, Japan), among others.

The etherified fatty alcohols used in the present invention have the general structural formula:

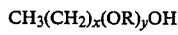

$$CH_3(CH_2)_x(OR)_yOH$$

wherein R is a straight chain alkyl group of from 2 to 4 carbon atoms, x is an integer from 15 to 23, and y is an integer from 2 to 100.

The glycol solvent component of the subject vehicle can be entirely propylene glycol, dipropylene glycol or polyethylene glycol (such as "PEG 200" (Dow Chemical) or a comparable polyethylene glycol solvent), or any combination thereof, provided that the total weight of glycol solvent equals from about 60 to about 90% of the total weight of the vehicle.

The etherified alcohol component of the vehicles of the present invention can comprise any combination of one or more etherified fatty alcohols, as defined above, said etherified fatty alcohols having a total chain length of from 20 to about 216 carbon atoms. "Total chain length" as used herein with respect to the etherified fatty alcohols is defined as the total number of carbon atoms in the etherified alcohols after etherification.

In addition to the principal glycol solvent and etherified fatty alcohol components, the subject vehicles may also include from about 0 to about 15% plasticizer material compatible with both the principal vehicle components and the active pharmaceutical agents which will be added to the vehicle. Suitable plasticizers include sorbitol, glycerol, polyethylene glycols having molecular weights of from 800 to 20,000, and the like. The plasticizer improves the plasticity and uniformity of the mixture of active agent and vehicle and enhances the spreadability of the vehicle.

Compatible plasticizers used with the subject invention do not cause separation of the principal components of the vehicle, i.e, the glycol and fatty alcohol components.

The vehicles of the present invention may also contain suitable coupling agents, including palmitic acid, stearic acid, behenic acid, fatty amides such as oleamide, palmitamide, stearamide, behenamide and esters of fatty acids having from 16 to 24 carbon atoms, such as polyethylene glycol monostearate, sorbitan monostearate, sorbitan sesquioleate and the corresponding monoesters of other fatty acids such as oleic acid and palmitic acid. One or more of these coupling agents may be present in the vehicle, with the total weight percentage of all coupling agents combined being from about 0 to about 15% of the total vehicle weight. The coupling agents help retard separation of the more liquid components of the vehicle upon prolonged storage at elevated temperatures.

The subject vehicles may optionally include from about 0 to about 20% by weight penetrants which increase the percutaneous absorption of topical pharmaceutical agents dispersed and/or dissolved in the vehicle. Because the glycol solvents of the subject vehicle, particularly propylene glycol, are excellent carriers of topical medicaments such as corticosteroids, the addition of penetrants is merely an optional feature of the present invention. Representative examples of penetrants include dimethylsulfoxide, dimethylacetanide and the like.

The topical vehicles of the present invention are substantially free of any unsaturated fatty alcohols and any fatty alcohols having less than 16 carbon atoms, as well as being substantially free of water and greasy substances such as mineral oil and petrolatum and preservatives such as parabens which have been known to cause hypersensitivity reactions.

Apart from the ingredients outlined above, the vehicles of the present invention may also include conventional, pharmaceutically accepted additives such as colorings, buffers or pH adjusters (e.g., citric acid), opacifiers, and other ingredients which are conventionally added to topical creams to improve or alter their pH, stability, appearance, feel, adherence to the skin, and so on.

Preferred ranges for the ingredients of the novel vehicles are from about 70 to about 85% glycol solvent, from about 5 to about 15% etherified fatty alcohol, from about 2 to about 8% plasticizer and from about 2 to about 8% coupling agent.

The vehicles of the present invention are prepared by combining the glycol solvent or solvents with the etherified fatty alcohol and, optionally, the compatible plasticizers, coupling agents and penetrants in a kettle equipped with agitation. The ingredients are heated with agitation to 60°–75° C. and then cooled to room temperature with continued mixing.

When it is desired to admix a topically active pharmaceutical ingredient with the subject vehicles, the ingredient may be added to the vehicle in powdered or liquid form and thoroughly admixed therewith with stirring and gradual heating until a thoroughly homogeneous mixture is formed. Topically active agents which can be effectively incorporated into a cream utilizing the novel cream vehicles of the present invention include, for example, antibiotics such as neomycin sulfate, polymyxin B sulfate, bacitracin, gramicidin and gentamicin sulfate; antifungal agents such as tolnaftate, benzoic acid, salicylic acid and nystatin; anti-inflammatory agents, particularly topical corticosteroids, including, e.g., fluocinonide, clobetasol propionate, halcinonide, betamethasone valerate, fluocinolone acetonide and triamcinolone acetonide; antihistamines such as chlorcyclizine hydrochloride, diphenhydramine hydrochloride and mepyramine maleate; antipruritics and local anesthetics such as Benzocaine and Lidocaine; and astringents such as tannins and aluminum salts.

The vehicles of the present invention are superior to prior art anhydrous cream vehicles for topical medicaments in a variety of respects. The popular, commercially utilized prior art anhydrous vehicles incorporate a fatty alcohol such as stearyl alcohol which is insoluble in propylene glycol and creates a cream-like structure in conjunction therewith. However, the substitution of an etherified fatty alcohol in the present invention increases the hydrophilic characteristics of the cream and enhances the water miscibility of the finished preparation, while performing the same physical function as a non-etherified fatty alcohol - namely, providing an opaque cream form for the vehicle. The increased water miscibility increases the angle of contact of the cream to the skin and enhances the ease of spreadability, greatly improving patient acceptance to topical products incorporating the subject vehicles.

Moreover, many forms of etherified fatty alcohols, for example, polyethylene glycol ethers of behenyl and stearyl alcohol, form a more occlusive film when applied to the skin than preparations containing only free, saturated fatty alcohols. This increased degree of occlusion promotes more rapid penetration of the active ingredient and, in the case of topical corticosteroids, better vasoconstrictor activity.

In addition, many etherified fatty alcohols can actually promote the solubility of the active ingredient in the glycol solvent, creating a more effective drug delivery system. For example, it has been discovered that polyethylene glycol ethers of behenyl alcohol, such as the NIKKOL BB series of products (Nikko Chemicals - Tokyo, Japan), help solubilize steroids in a propylene glycol-containing base. On the other hand, the free saturated fatty alcohols in the prior art anhydrous vehicles do not promote the solubilization of active ingredients in the glycol solvent.

In addition to the foregoing advantages, the subject cream vehicles can incorporate a higher weight concentration of glycol solvent than prior art anhydrous creams, which generally contain no more than a maximum of 70-80% glycol solvent. Because of the greater efficiency of etherified fatty alcohols in maintaining cream vehicle consistency with glycol solvents in comparison with free fatty alcohols, a lower percentage of the etherified fatty alcohols is required in the vehicle, permitting up to a maximum of 90% glycol solvent. It is well known in the pharmaceutical arts that the higher the concentration of glycol solvent, particularly propylene glycol, the less need there is for added preservatives to inhibit bacterial and fungal deterioration because of the antimicrobial properties of the glycol. Moreover, because the glycol solvent is the principal delivery vehicle for the active ingredient, more effective and rapid release of the active ingredient to the site of action can be obtained in most instances with an increased concentration of glycol solvent in the vehicle.

The cream vehicles of the present invention, like the known anhydrous cream vehicles, can be used in conjunction with pharmaceutical agents that are adversely effected by the presence of water in the vehicle, and yet are highly water-miscible so that they are nonstaining, are water-washable, and interact with moisture in the skin for ease of spreadability and to provide an occlusive film. Furthermore, the anhydrous vehicles provide a medium to readily absorb fluid discharge from skin lesions, wounds, and so on.

The subject cream vehicles can be used in a variety of applications other than for topically applied prescription pharmaceutical products. For example, these vehicles are suitable for use with over-the-counter skin treatment preparations of the drug and cosmetic types, including medicated and non-medicated skin creams, suntan and sunscreen preparations, blemish treatments and the like. Moreover, because of their emollience and excellent spreadability, the subject vehicles are also well adapted for use as cosmetic bases with the addition of suitable coloring agents and other conventional cosmetic additives. Because of their hypoallergenic and non-irritating nature, the novel vehicles can be used by the great majority of individuals even on sensitive skin areas without adverse effect.

The novel cream vehicles disclosed herein have a long shelf life without becoming hydrolyzed, rancid, or moldy. The vehicles are also stable (i.e., the components do not separate) even after being stressed up to 47° C.

The following Examples will provide detailed illustrations of methods of producing the anhydrous vehcles according to the present invention as well as topical pharmaceutical compositions incorporating active ingredients in thos vehicles. Moreover, data will be given with regard to clinical testing performed with topical medicaments comprising the novel vehicles which demonstrate their effectiveness and safety. These Examples are not intended, however, to limit or restrict the scope of the invention in any way, and should not be construed as providing conditions, parameters, ingredients or starting materials which must be utilized exclusively in order to practice the present invention.

In all of the following Examples which deal with the preparation of the novel anhydrous cream vehicles, the ingredients were combined in a stainless steel jacketed kettle equipped with agitation and agitated while heating to 60° C. until a uniform homogeneous creamy mixture was obtained:

| Ingredients | Weight (grams) | |
| --- | --- | --- |
| | Ex. 1 | Ex. 2 |
| Propylene glycol USP | 89.95 | 67.95 |
| BRIJ 700 (polyoxyethylene stearyl ether*, ICI Americas, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

*Steareth 100 (CTFA nomenclature)

Examples 3–4

| Ingredients | Weight (grams) | |
| --- | --- | --- |
| | Ex. 3 | Ex. 4 |
| Propylene glycol USP | 85.95 | 67.95 |
| BRIJ 72 (polyoxyethylene stearyl ether*, ICI Americas, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

*Steareth 2 (CTFA nomenclature)

Examples 5-6

| Ingredients | Weight (grams) | |
|---|---|---|
| | Ex. 5 | Ex. 6 |
| Propylene glycol USP | 85.95 | 67.95 |
| EUMULGIN B-3 (polyethylene glycol cetyl/stearyl ether**, HENKEL) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

**Ceteareth 30 (CTFA nomenclature)

Examples 7-8

| Ingredients | Weight (grams) | |
|---|---|---|
| | Ex. 7 | Ex. 8 |
| Propylene glycol USP | 85.95 | 67.95 |
| BRIJ 58 (polyethylene glycol, cetyl ether***, ICI Americas, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

***Ceteth 20 (CTFA nomenclature)

Example 9-10

| Ingredients | Weight (grams) | |
|---|---|---|
| | Ex. 9 | Ex. 10 |
| Propylene glycol USP | 85.95 | 67.95 |
| PROCAL CA-2 (polyoxyethylene glycol cetyl ether*, Protameen Chemicals, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid | 1 | 1 |

*Ceteth 2 (CFTA nomenclature)

Example 11-12

| Ingredients | Weight (grams) | |
|---|---|---|
| | Ex. 11 | Ex. 12 |
| Propylene glycol USP | 85.95 | 67.95 |
| PROCAL CA-30 (polyethylene glycol cetyl ether**, Protameen Chemicals, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

**Ceteth 30 (CFTA nomenclature)

Example 13-14

| Ingredients | Weight (grams) | |
|---|---|---|
| | Ex. 13 | Ex. 14 |
| Propylene glycol USP | 85.95 | 67.95 |
| NIKKOL BB-5 (polyethylene glycol behenyl ether***, Nikko Chemicals) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

***Beheneth 5 (CFTA nomenclature)

Examples 15-16

| Ingredients | Weight (grams) | |
|---|---|---|
| | Ex. 15 | Ex. 16 |
| Propylene glycol USP | 85.95 | 67.95 |
| NIKKOL BB-10 (polyethylene glycol behenyl ether*, Nikko Chemicals) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

*Beheneth 10 (CFTA nomenclature)

Example 17-19

| Ingredients | Weight (grams) | | |
|---|---|---|---|
| | Ex. 17 | Ex. 18 | Ex. 19 |
| Propylene glycol USP | 85.95 | 67.95 | 81.95 |
| NIKKOL BB-20 (polyethylene glycol behenyl ether**, Nikko Chemicals) | 2 | 20 | 6 |
| PEG 8000 (polyethylene glycol, Dow Chemical Co.) | 8 | 8 | 8 |
| ARLACEL 60 (sorbitan monostearate, ICI Americas, Inc.) | 3 | 3 | 3 |
| Stearic acid NF | 1 | 1 | 1 |

**Beheneth 20 (CFTA nomenclature)

Examples 20-21

| Ingredients | Weight (grams) | |
|---|---|---|
| | Ex. 20 | Ex. 21 |
| Propylene glycol USP | 85.95 | 67.95 |
| NIKKOL BB-30 (polyethylene glycol behenyl ether***, Nikko Chemicals) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

***Beheneth 30 (CFTA nomenclature)

Examples 22-23

| Ingredients | Weight (grams) | |
|---|---|---|
| | Ex. 22 | Ex. 23 |
| Propylene glycol USP | 50 | 74.95 |
| NIKKOL BB-5 | 6 | 6 |
| PEG 8000 (polyethylene glycol, Dow Chemical Co.) | 39.95 | 15 |
| ARLACEL 60 (sorbitan monostearate, ICI Americas, Inc.) | 3 | 3 |
| Stearic acid NF | 1 | 1 |

Example 24-25

| Ingredients | Weight (grams) Ex. 24 | Ex. 25 |
| --- | --- | --- |
| Propylene glycol USP | 90 | 89.95 |
| NIKKOL BB-5 | 5.95 | 6 |
| ARLACEL 60 (sorbitan monostearate ICI Americas, Inc.) | 3 | 3 |
| Stearic acid NF | 1 | 1 |

Examples 26-27

| Ingredients | Weight (grams) Ex. 26 | Ex. 27 |
| --- | --- | --- |
| Propylene glycol USP | 83.95 | 55.95 |
| NIKKOL BB-5 | 6 | 6 |
| PEG 8000 (polyethylene glycol, Dow Chemical Co.) | 8 | 8 |
| ARLACEL 60 (sorbitan monostearate, ICI Americas, Inc.) | 1 | 15 |
| Stearic acid NF | 1 | 15 |

Examples 28-29

| Ingredients | Weight (grams) Ex. 28 | Ex. 29 |
| --- | --- | --- |
| Propylene glycol USP | 85.95 | 67.95 |
| EUMULGIN B-3 (polyethylene glycol) cetyle/stearyl ether*, Henkel Corp. | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

*Ceteareth 30 (CFTA nomenclature)

Examples 30-31

| Ingredients | Weight (grams) Ex. 30 | Ex. 31 |
| --- | --- | --- |
| Propylene glycol USP | 85.95 | 67.95 |
| MACOL CSA-2 (polyethylene glycol cetyl/stearyl ether**, Mazer Chemicals, Inc.) | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

**Ceteareth 2 (CFTA nomenclature)

Examples 32-33

| Ingredients | Weight (grams) Ex. 32 | Ex. 33 |
| --- | --- | --- |
| PEG 200 (polyethylene glycol, Dow Chemical Co.) | 85.95 | 67.95 |
| NIKKOL BB-20 | 2 | 20 |
| PEG 8000 (polyethylene glycol, Dow Chemical Co.) | 8 | 8 |
| ARLACEL 60 (sorbitan monostearate, ICI Americas, Inc.) | 3 | 3 |
| Stearic acid NF | 1 | 1 |

EXAMPLE 34

Each of the anhydrous vehicles prepared according to Examples 1 through 33 was combined with a topically active steroid, fluocinonide USP (21-(acetyloxy)-6α,9-difluoro-11β-hydroxy-1α,17-[(1-methylethylidene)bis(oxy)]pregna-1,4-diene-3,20dione) by removing about 5% of each cream vehicle and slurrying with 0.05 grams of fluocinonide. The slurry was then transferred back to the main mixing kettle and circulated with good agitation for about one hour until a homogeneous moisture of cream and active ingredient was achieved.

Alternatively, the active ingredient can be dissolved in a small amount of propylene glycol (e.g., about 5% of the total vehicle weight) and then added to the vehicle.

As may be seen from the above Examples, the preparation of the subject anhydrous cream vehicles is quite simple and can be accomplished by any commercially feasible conventional methods for mixing and heating the components of the vehicles. These novel vehicles are highly water miscible to enable easy removal from skin and clothing. They also provide a good occlusive film and a high degree of percutaneous absorption of active ingredient, improving therapeutic efficiency.

It Will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims.

1. An anhydrous, water-miscible, water-washable, non-irritating vehicle for topical use, said vehicle having a cream-like consistency and comprising, in combination:
   (a) from about 70 to about 85% by weight of at least one glycol solvent;
   (b) from about 2 to about 15% by weight etherified saturated fatty alcohol, said etherified alcohol having a total chain length of from 46 to 82 carbon atoms and having the structural formula $CH_3(CH_2)_x(OR)_yOH$ wherein R is —$CH_2CH_2$—, x is an integer from 15 to 21, and y is an integer from 15 to 30;
   (c) from about 0 to about 15% by weight compatible plasticizer;
   (d) from about 0 to about 15% by weight compatible coupling agent; and
   (e) from about 0 to about 10% penetrant, said vehicle being substantially free of water, greasy substances, unsaturated fatty alcohols and fatty alcohols having less than 16 carbon atoms.

2. A vehicle according to claim 1 which comprises from about 2 to about 6% etherified fatty alcohol.

3. A vehicle according to claim 1, wherein said glycol solvent is selected from the group consisting of propylene glycol, dipropylene glycol and polyethylene glycol.

4. A vehicle according to claim 3, wherein said polyethylene glycol has a molecular weight from about 200 to about 800.

5. A vehicle according to claim 1, wherein said etherified fatty alcohol is selected from the group consisting of etherified cetyl, etherified stearyl and etherified behenyl alcohols.

6. A vehicle according to claim 1, wherein said etherified fatty alcohol is a polyoxyethylene or polyethylene glycol ether of a saturated fatty alcohol, said saturated alcohol having from 16 to 22 carbon atoms.

7. A vehicle according to claim 1 which comprises from about 2 to about 8% by weight compatible plasticizer, and from about 2 to about 8% by weight compatible coupling agent.

8. A vehicle according to claim 1, wherein said plasticizer comprises one or more ingredients selected from the group consisting of sorbitol, glycerol and polyethylene glycols having a molecular weight from about 800 to about 20,000.

9. A vehicle according to claim 1, wherein said coupling agent comprises one or more ingredients selected from the group consisting of palmitic acid, stearic acid, behenic acid, and the amides, sorbitan esters and polyethylene glycol esters of saturated fatty acids having 16 to 24 carbon atoms.

10. A vehicle according to claim 6, wherein said etherified fatty alcohol is a polyethylene glycol ether of behenyl alcohol, cetyl alcohol or stearyl alcohol.

11. A vehicle according to claim 3, wherein said glycol solvent is propylene glycol.

12. A vehicle according to claim 4, wherein said glycol solvent comprises a polyethylene glycol having a molecular weight of about 200.

13. A vehicle according to claim 10, wherein said glycol solvent is propylene glycol, said plasticizer is a polyethylene glycol having a molecular weight of about 8000 and said coupling agent comprises stearic acid and sorbitan monostearate.

14. A topical medicament which comprises a vehicle according to claim 1, admixed with a topically active pharmaceutical agent.

15. A topical medicament according to claim 14, Wherein said pharmaceutical agent is selected from the group consisting of antibiotics, antifungal agents, anti-inflammatory agents, antihistamines, local anesthetics and astringents.

16. A topical medicament according to claim 15, wherein said topical agent is an anti-inflammatory corticosteroid.

17. A topical medicament according to claim 16, wherein said corticosteroid is fluocinonide.

18. A vehicle according to claim 13, wherein said saturated alcohol is about 2% benhenyl alcohol by weight.

19. A vehicle according to claim 13, wherein said saturated alcohol is about 6% behenyl alcohol by weight.

20. A vehicle according to claim 18, wherein y=20.

21. A vehicle according to claim 19, wherein y=20.

22. A topical medicament according to claim 17, wherein said saturated alcohol is from about 2 to about 6% behenyl alcohol by weight.

* * * * *